United States Patent

Bennett et al.

[11] Patent Number: 6,043,245
[45] Date of Patent: Mar. 28, 2000

[54] TETRAHYDROFURAN ANTIFUNGAL PHOSPHATE

[75] Inventors: Frank Bennett, Piscataway; Viyyoor M. Girijavallabhan, Parsippany; Naginbhai M. Patel, Piscataway; Anil K. Saksena; Ashit Ganguly, both of Upper Montclair, all of N.J.

[73] Assignee: Schering Corporation, Kenilworth, N.J.

[21] Appl. No.: 09/160,997

[22] Filed: Sep. 25, 1998

Related U.S. Application Data

[60] Provisional application No. 60/060,678, Sep. 25, 1997.

[51] Int. Cl.⁷ ............... A61K 31/496; A61K 31/675; C07D 405/14; C07F 9/6509
[52] U.S. Cl. ............... 514/252; 514/85; 544/337; 544/366
[58] Field of Search ............... 544/366; 514/252

[56] References Cited

U.S. PATENT DOCUMENTS

| | | | |
|---|---|---|---|
| 5,661,151 | 8/1997 | Saksena et al. | 514/252 |
| 5,693,626 | 12/1997 | Saksena et al. | 514/85 |
| 5,703,079 | 12/1997 | Saksena et al. | 514/252 |
| 5,710,154 | 1/1998 | Saksena et al. | 514/252 |
| 5,714,490 | 2/1998 | Saksena et al. | 514/252 |

FOREIGN PATENT DOCUMENTS

95/17407 6/1995 WIPO .

*Primary Examiner*—Emily Bernhardt
*Attorney, Agent, or Firm*—Thomas D. Hoffman

[57] ABSTRACT

A compound of the formula I wherein G is H or $PO_3H_2$ or a pharmaceutical acceptable salt thereof, pharmaceutical compositions containing such compounds and method of using such compounds or pharmaceutical compositions containing them to treat or prevent fungal infection are disclosed.

5 Claims, No Drawings

TETRAHYDROFURAN ANTIFUNGAL PHOSPHATE

This application claims the benefit of U.S. Provisional Application No. 60/060,678, filed Sep. 25, 1997.

BACKGROUND OF THE INVENTION

This invention relates to a tetrahydrofuran antifungal phosphate which is named: 5-[[2(S)-[4-[4-[4-[4-[[(R-cis)-5-(2,4-difluorophenyl)-tetrahydro-5-(1H-1,2,4-triazol-1-ylmethyl)-3-furanyl] methoxy]phenyl]-1-piperazinyl] phenyl]-4,5-dihydro-5-oxo-1H-1,2,4-triazol-1-yl]-1(S)-methylbutyl]oxy]-5-oxobutyl phosphate, and to a tetrahydrofuran antifungal butyrate which is named: (−)-2 (S)-[4-[4-[4-[4-[[(R-cis)-2-(2,4-difluorophenl) tetrahydro-2-(1H-1,2,4-triazol-1-ylmethyl)-4-furanyl]methoxy]phenyl]-1-piperazinyl]phenyl]-4,5-dihydro-5-oxo-1H-1,2,4-triazol-1-yl]-1(S)-methylbutyl 4-hydroxybutanoate and pharmaceutically acceptable salts thereof, pharmaceutical compositions containing such antifungals and methods of treating or preventing fungal infections in hosts using them.

International Publication Nos. WO 96/38443 (published Dec 5, 1996) and WO 95/17407 (published Jun. 29, 1995) disclose various tetrahydrofuran antifungals and phosphate esters thereof but neither one discloses the tetrahydrofuran antifungal compounds of the present invention.

There is a need for a broad spectrum antifungal agent having solubility suitable for parenteral administration and a favorable activity profile for treating and/or preventing systemic fungal infections, especially Aspergillus, Candida, Cyrptococcus and opportunistic infections.

SUMMARY OF THE INVENTION

The present invention also provides a compound represented by the formula I

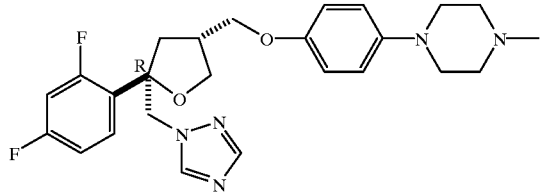

I

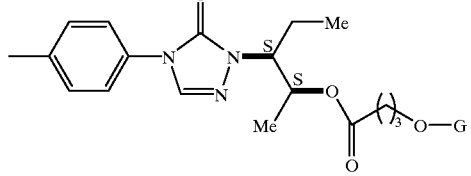

wherein G is H or $PO_3H_2$ or a pharmaceutically acceptable salt thereof.

The present invention provides a compound represented by the formula II

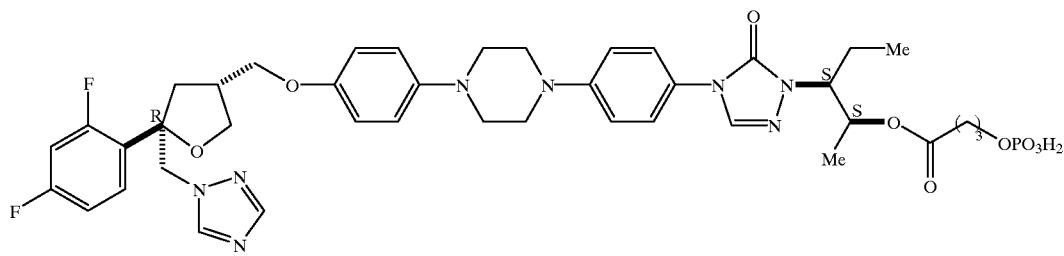

II or a pharmaceutically acceptable salt thereof.

The present invention provides a compound represented by formula III

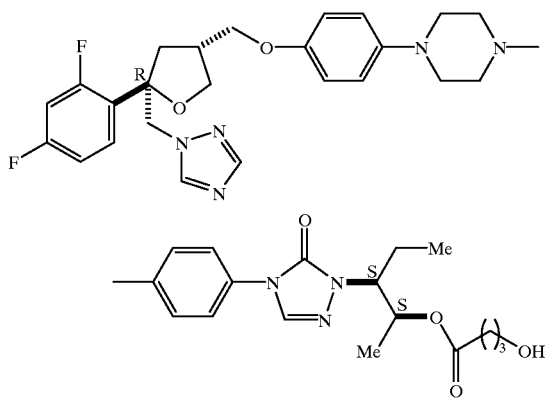

III or a pharmaceutically acceptable salt thereof.

DETAILED DESCRIPTION OF THE INVENTION AND OF THE PREFERRED EMBODIMENTS

The compound of the present invention of formula II in the form of a pharmaceutically acceptable salt such as the di N-methylglucamine ("NMG") salt represented by formula II.2NMG is a water soluble prodrug which is converted in vivo into the active metabolite III which is also converted in vivo into the antifungal agent represented by formula IV according to the following equations:

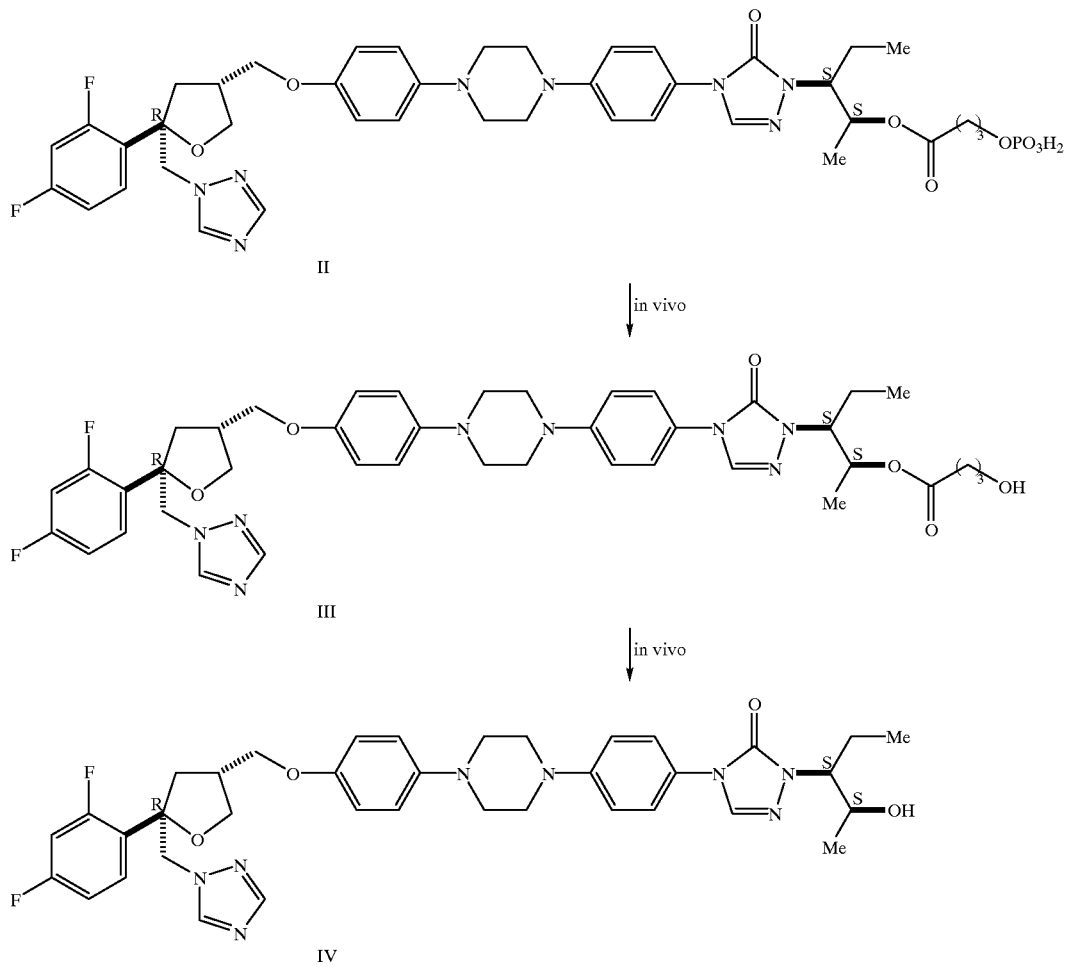

The compound of formula II hydrolyzes in vivo to the compound of formula III; III then hydrolyzes in vivo to the compound of formula IV. The hydrolysis of II to III occurs primarily in the serum and in tissues (liver, lung and kidney). The hydrolysis of III to IV occurs primarily in the serum.

The compound of formula II upon intravenous administration to mice in the form of its di-NMG salt represented by formula II.2NMG in water provides superior blood levels of the compound of formula IV in mice. See Tables 1–3.

When an aqueous solution of the di-NMG salt of the compound of formula II (II.2NMG )was administered intravenously to mice in a side-by-side comparison with the di-NMG salt of the compound of formula V (disclosed in WO 95/17407 at the lower right hand corner of page 15), the pharmacokinetic parameters of the compound of formula IV derived from the di-NMG salt of the compound of formula the II of this invention were unexpectedly superior to those of the compound of formula IV derived from the di-NMG salt of the prior art compound of formula V. The results are summarized in Table 3

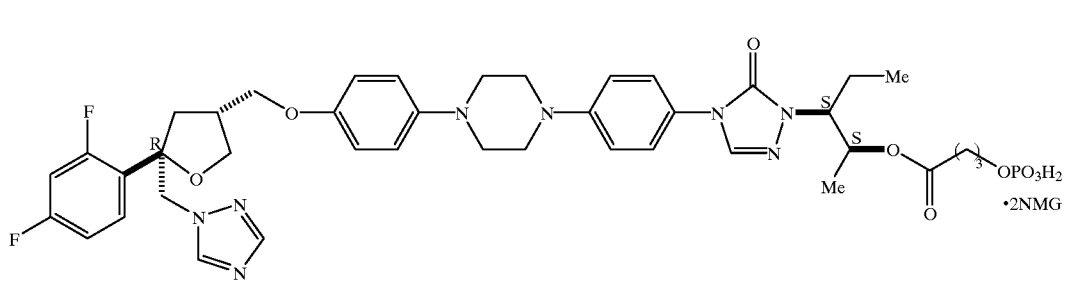

II.2NMG

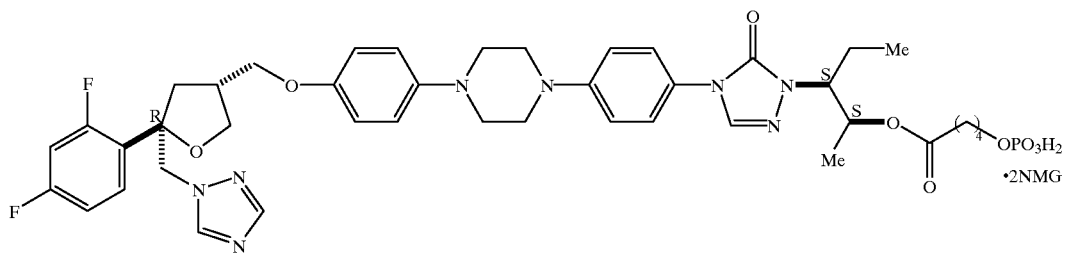

TABLE 1

Concentrations of the compound of formula IV in pooled mouse[1] plasma (2 mice/pool) following intravenous administration of a 20 mg/kg of the compound of formula IV dose equivalent of the di-NMG salt of the compound of this invention represented by the formula II in sterile water.

| | μg/ml | | | |
|---|---|---|---|---|
| hr | Pool 1 | Pool 2 | Mean | % CV[3] |
| 0 (undosed) | 0.000[2] | 0.000 | 0.000 | |
| 0.017 (1 min) | 0.171 | 0.164 | 0.168 | 2.95 |
| 0.05 (3 min) | 0.378 | 0.297 | 0.338 | 16.9 |
| 0.083 (5 min) | 0.798 | 0.817 | 0.808 | 1.66 |
| 0.25 (15 min) | 1.57 | 2.72 | 2.15 | 37.9 |
| 0.5 (30 min) | 3.02 | 2.34 | 2.68 | 17.9 |
| 1 hr. | 4.46 | 3.95 | 4.21 | 8.58 |
| 3 hr. | 5.16 | 5.63 | 5.40 | 6.16 |
| 6 hr. | 5.96 | 3.59 | 4.78 | 35.1 |
| 24 hr. | 0.915 | 0.992 | 0.954 | 5.71 |
| Cmax (μg/ml) | | | 5.40 | |
| Tmax (hr) | | | 3 | |
| AUC (0–24 hr) (μg.hr/ml) | | | 79.1 | |

[1]Male Charles River mice having an average body weight of 18–20 g obtained from Charles River, Wilmington, MA 01887
[2]Values below the lower limit of quantitation of 0.05 μg/ml are reported as zero.
[3]% CV is percent coefficient of variation which is a relative measure of variability. See Steele and Torrie, "Principles and Procedures of Statistics", (1980) 2nd Edition, McGraw-Hill, NY, at page 27.

TABLE 2

Concentrations of the compound of formula IV in pooled mouse[1] plasma (2 mice/pool) following intravenous administration of a 20 mg/kg of compound of formula IV dose equivalent of the di-NMG salt of the compound of the prior art represented by formula V in sterile water.

| | μg/ml | | | |
|---|---|---|---|---|
| hr | Pool 1 | Pool 2 | Mean | % CV[4] |
| 0 (undosed) | 0.000[1] | 0.000 | 0.000 | — |
| 0.017 (1 min) | 0.000 | 0.000 | 0.000 | — |
| 0.05 (3 min) | 0.738 | 0.663 | 0.723 | 11.7 |
| 0.083 (5 min) | 1.04 | 1.43 | 1.24 | 22.3 |
| 0.25 (15 min) | 1.22 | 0.407 | 0.814 | 70.6 |
| 0.5 (30 min) | 1.99 | —[3] | 1.99 | — |
| 1 hr. | 2.73 | 2.63 | 2.68 | 2.64 |
| 3 hr. | 0.923 | 2.51 | 1.72 | 65.4 |
| 6 hr. | 2.59 | 1.90 | 2.25 | 21.7 |
| 24 hr. | 0.447 | 0.515 | 0.481 | 10.0 |
| Cmax (μg/ml) | | | 2.68 | |
| Tmax (hr) | | | 1 | |
| AUC (0–24 hr) (μg.hr/ml) | | | 36.7 | |

[1]Male Charles River mice having an average body weight of 18–20 g obtained from Charles River, Wilmington, MA 01887
[2]Values below the lower limit of quantitation of 0.05 μg/ml are reported as zero.
[3]Connection between detector and computer was lost; therefore this value was lost.
[4]% CV is percent coefficient of variation which is a relative measure of variability. See Steele and Torrie, "Principles and Procedures of Statistics", (1980) 2nd Edition, McGraw-Hill, NY, at page 27.

TABLE 3

PHARMACOKINETIC ("PK") PARAMETERS OF THE COMPOUND OF FORMULA IV IN MOUSE[1] PLASMA FOLLOWING INTRAVENOUS ADMINISTRATION OF 20 MG/KG OF COMPOUND OF FORMULA IV DOSE EQUIVALENT OF THE DI-NMG SALTS OF THE COMPOUNDS OF FORMULAS II AND V IN STERILE WATER TO MICE.

PK Parameters of the Compound of Formula IV

| Compound Administered | $C_{max}$ (μg/mL) | $T_{max}$ (hr) | AUC[2] (μg.hr/min) | Bioavailability (%) |
|---|---|---|---|---|
| Formula II.2 NMG | 5.40 | 3 | 79.1 | 65 |
| Formula V.2 NMG | 2.68 | 1 | 36.7 | 30 |

[1]Male Charles River mice having an average body weight of 18–20 g obtained from Charles River, Wilmington, MA 01887.
[2]Area under the curve measured form time zero to 24 hrs. in (μg.hr/min).

Table 3 summarizes and compares the pharmacokinetic parameters listed in Tables 1 and 2. The pharmacokinetic parameters for the compound of formula IV derived from the di-NMG salt of the compound of the present invention (II.2NMG) are superior to the pharmacokinetic values for the compound of formula IV derived from the di-NMG salt of the prior art compound of formula V.

The pharmacokinetic parameters of the compound of formula IV obtained upon analysis of mouse plasma from mice intravenously injected with the compound of the present invention represented by formula II of this invention were surprisingly unexpectedly superior to those obtained from mouse plasma from mice intravenously injected with the compound of the prior art represented by formula V (see Tables 1–3).

The term "opportunistic fungi" include Cryptococcus, Histoplasma, Blastomyces, Coccidioides, Fusarium, Mucor, Paracoccidioides, Fonsecaea, Wangiella, Sporothrix, Pneumocystis, Trichosporon as shown by in vitro and/or in vivo activity in an appropriate animal species e.g. mouse, rat or rabbit. The compounds of the invention is expected to exhibit activity against many genera and species of protoza, bacteria, gram negatives, gram positives, anaerobes, including Legionella Borrelia, Mycoplasma, Treponema, Gardnerella, Trichomonas and Trypanosoma.

The compounds of this invention represented by formulas I–III are expected to exhibit broad spectrum antifungal activity against human and animal pathogens, such as the following: Aspergillus, Blastomyces, Candida, Cryptococcus, Coccidioides, Epidermophyton, Fonsecaea, Fusarium, Mucor, Saccharomyces, Torulopsis, Trichophyton, Trichosporon, Sporothrix and Pneumocystis.

The compounds of formulas III and IV- the in vivo conversion products of the compound of formula II-exhibit antifungal activity in in vivo tests in mice and such activity is unexpectedly better than that of existing antifungal agents e.g. itraconazole and fluconazole as well as that of the azole compounds specifically disclosed by Saksena et al. in U.S. Pat. No. 5,039,676 and International Publication No. WO 93/09114.

The in vitro anti-fungal activities of the compounds of the formulas II, III and IV against forty-one species of Candida, thirty species of Aspergillus and nine species of Cryptococcus are summarized in Table 5. Based on a comparison of the geometric mean MICs (mcg/mL), the in vitro antifungal activities of the compounds of the formulas III and IV are similar to one another; the in vitro activity of II is much lower. The compound of formula II showed good in vivo activity in two mice models. Doses of 10 mg/kg of II provided 100% survival at day 9 in mice with a systemic *Candida albicans* infection and 70% survival in mice with a pulmonary *Aspergillus fumigatus* infection; fluconazole is inactive in this Aspergillus pulmonary infection model in mice. This Aspergillus pulmonary infection model in mice was performed in accordance with the procedures of David Loebenberg et al. entitled "In vitro and in vivo activity of Sch 42427, the active enantiomer of the antifungal agent Sch 39304" published in *Antimicrobial Agents and Chemotherapy* (1992), Vol. 36, pp. 498–501.

Pharmacokinetic studies in human tissues and serum indicated that the compound of formula II is metabolized to the compound of formula IV via the metabolite represented by formula III. Plasma levels in cynomologus monkeys following intravenous (IV) infusion of the compound of formula II as the di NMG salt show the following pharmokinetic (PK) profile summarized in Table 4.

TABLE 4

Cynomolgus Monkey PK Levels Following Intravenous Infusion of II.2 NMG

| Compound | $C_{max}$(μg/mL) | AUC[1] |
|---|---|---|
| II | 40.7 | 3.98 |
| III | 4.8 | 4.41 |
| IV | 1.04 | 24.11 |

[1]The area under the curve measured from time zero to 48 hours, i.e., AUC (0–48 hrs) in μg.hr/mL.

The antifungal compounds of formulas I–III and pharmaceutical compositions of these compounds are expected to exhibit anti-allergic, anti-inflammatory and immunomodulating activities, broad spectrum antiinfective activity, e.g., antibacterial, antiprotozoal and antihelminthic activities in mammals, especially man.

The present invention also provides a composition for treating or preventing fungal infections comprising an antifungally effective amount of the compound represented by formula I or a pharmaceutically acceptable salt thereof and a pharmaceutically acceptable carrier or diluent therefor.

The pharmaceutical compositions of the present invention may also contain a fungicidally effective amount of other antifungal compounds such as cell wall active compounds. The term "cell wall active compound", as used herein, means any compound that interferes with the fungal cell wall and includes, but is not limited to, compounds such as papulacandins, echinocandins, and aculeacins as well as fungal cell wall inhibitors such as nikkomycins, and others which are described in U.S. Pat. No. 5,006,513 which is hereby incorporated by reference.

TABLE 5

In Vitro Antifungal Activity(mcg/mL)

| Compound | Microorganisms | G mean MICs[1] | Range |
|---|---|---|---|
| II | Aspergillus [2] species (n = 30) | 5.9 | 0.5 to >32 |
|  | Candida [3] | 7.5 | 1 to >32 |
| II | species (n = 41) [2] |  |  |
| II | Cryptococcus [3] neoformans (n = 9) [3] | 1.9 | 0.125 to 32 |
|  | Aspergillus [2] | 0.2 | 0.0313 to 2 |
| III | species (n = 30) |  |  |
| III | Candida [3] species (n = 41) | 0.3 | ≦0.0156 to 8 |
| III | Cryptococcus [3] neoformans (n = 9) | 0.09 | 0.0156 to 0.5 |
| IV | Aspergillus [2] species (n = 30) | 0.1 | ≦0.0156 to 1 |
| IV | Candida [3] species (n = 41) | 0.2 | ≦0.0156 to 8 |
| IV | Cryptococcus [3] neoformans (n = 9) | 0.04 | ≦0.0150 to 0.5 |

[1]Geometric means MICs
[2] In vitro activity against Aspergillus measured in accordance with Espinel-Ingroff's Methodology
[3] In vitro activity measured in accordance with procedures for NCCLS standard M27A.

The pharmaceutically acceptable salts of the compounds of the present invention include pharmaceutically acceptable basic addition salts.

The pharmaceutically acceptable bases found suitable for use in the present invention are those which form pharmaceutically acceptable salts of the acidic antifungal compounds of formulas I or II and include suitable organic and inorganic bases. Suitable organic bases include primary, secondary and tertiary alkyl amines, alkanolamines, aromatic amines, alkylaromatic amines and cyclic amines. Exemplary organic amines include the pharmaceutically acceptable bases selected form chloroprocaine, procaine, piperazine, glucamine, N-methylglucamine, N,N-dimethylglucamine ethylendediamine, diethanolamine, diisopropylamine, diethylamine, N-benzylenediamine, diethanolamine, diisopropylamine, diethylamine, N-benzyl- 2-phenylethylamine, N,N'-dibenzylethylenediamine, choline, clemizole, triethylamine ("Et$_3$N"), tris (hydroxymethyl)aminomethane, or D-glucosamine. The preferred organic bases include N-methylglucamine ("NMG"), diethanolamine, and tris(hydroxymethyl) aminomethane ("TRIS"). Use of two equivalents of NMG in this invention is more preferred. The suitable inorganic bases also include alkali metal hydroxides such as sodium hydroxide.

The pharmaceutical compositions of the present invention may be adapted for any mode of administration e.g., for oral, parenteral, e.g., SC, IM. IV and IP, topical or vaginal administration or by inhalation (orally or intranasally) Such compositions are formulated by combining the compound of formula II or one or two equivalents of a pharmaceutically base, e.g. NMG to form a acceptable salt of the formula II.2NMG with a suitable, inert, pharmaceutically acceptable carrier or diluent.

Examples of suitable compositions include solid or liquid compositions for oral administration such as tablets, capsules, pills, powders, granules, solutions, suppositories, troches, lozenges, suspensions or emulsions. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet, the active compound is mixed with carrier having the necessary binding properties in suitable proportions and compacted in the shape and size desired.

Topical dosage forms may be prepared according to procedures well known in the art, and may contain a variety of ingredients, excipients and additives. The formulations for topical use include ointments, creams, lotions, powders, aerosols, pessaries and sprays.

For preparing suppositories, a low melting wax such as a mixture of fatty acid glycerides or cocoa butter is first melted, and the active ingredients are dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution with an appropriate amount of a hydroxypropyl α- β or -γ-cyclodextrin having 2 to 11 hydroxypropyl groups per molecule of cyclodextrin, polyethylene glycol, e.g., PEG-200 or propylene glycol, which solutions may also contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water. A particularly preferred aqueous pharmaceutical composition may be prepared from the compound of formula I together with hydroxypropyl-β-cyclodextrin in water. The use of derivatives of α-, β- and γ-cyclodextrins, for example, hydroxpropyl-β-cyclodextrin are disclosed by N. Bodor U.S. Pat. No. 4,983,586, Pitha U.S. Pat. No. 4,727,064 and Janssen Pharmaceutical International Patent Application No. PCT/EP 84/00417.

The pharmaceutical compositions of the present invention may be prepared by admixing the pharmaceutically acceptable carrier, e.g., a hydroxypropyl-β-cyclodextrin in water, and adding thereto an antifungally effective amount of the compound of the present invention. The solution so formed is filtered, and optionally, the water may be removed by well known methods, e.g., rotatory evaporation or lyophilization. The formation of the solution may take place at a temperature of about 15° to 35° C. The water is normally sterilized water and may also contain pharmaceutically acceptable salts and buffers, e.g., phosphate or citrate as well as preservatives. The molar ratio of the antifungal compound of formula I to hydroxpropyl-β-cyclodextrin is about 1:1 to 1:80, preferably 1:1 to 1:2. Normally the hydroxypropyl-β- is present in molar excess.

Also included are solid form preparations which are intended to be converted, shortly before use, into liquid form preparations for either oral or parenteral administration. The solid form preparations intended to be converted to liquid form may contain, in addition, to the active materials, such as compounds of this invention, and optionally a cell wall active compound, especially a fungal cell wall inhibitor, e.g., a nikkomycin, flavorants, colorants, stabilizers, buffers, artificial and natural sweeteners, dispersants, thickeners, solubilizing agents and the like. The solvent utilized for preparing the liquid form preparations may be water, isotonic water, ethanol, glycerin, polyethylene glycols, propylene glycol, and the like, as well as mixtures thereof.

Parenteral forms to be injected intravenously, intramuscularly, or subcutaneously are usually in the form of a sterile solution, and may contain salts or glucose to make the solution isotonic.

The topical dosage for humans for antifungal use in the form of a pharmaceutical formulation comprising a compound of formula I (usually in the concentration in the range from about 0.1% to about 20% preferably from about 0.5% to about 10% by weight) together with a non-toxic, pharmaceutically acceptable topical carrier, is applied one or more times daily to the affected skin until the condition has improved.

In general, the oral dosage for humans for antifungal use ranges from about 1 mg per kilogram of body weight to about 30 mg per kilogram of body weight per day, in single or divided doses, with about 1 mg per kilogram of body weight to about 20 mg per kilogram of body weight per day being preferred and the dose of about 1 mg per kilogram of body weight to about 10 mg per kilogram of body weight per day being most preferred.

In general, the parenteral dosage for humans for antifungal use ranges from about 1 mg per kilogram of body weight per day to about 30 mg per kilogram of body weight per day, in single or divided doses, with about 1 to about 20 mg per kilogram of body weight per day being preferred and the dose of about 1 mg per kilogram of body weight to about 8 mg per kilogram of body weight per day in single or divided doses being most preferred.

Intravenous (IV) infusion is the preferred mode of administration. Single or divided doses of 200–450 mg twice a day by IV infusion are preferred. Doses of 200–250 mg twice a day by IV infusion are most preferred The exact amount, frequency and period of administration of the compounds of the present invention for antifungal use will vary, of course, depending upon the sex, age and medical condition of the patient as well as the severity of the infection as determined by the attending clinician.

EXPERIMENTAL

EXAMPLE 1

A preparation of the compound of formula II and the salt of formula II.2NMG

Step (A)

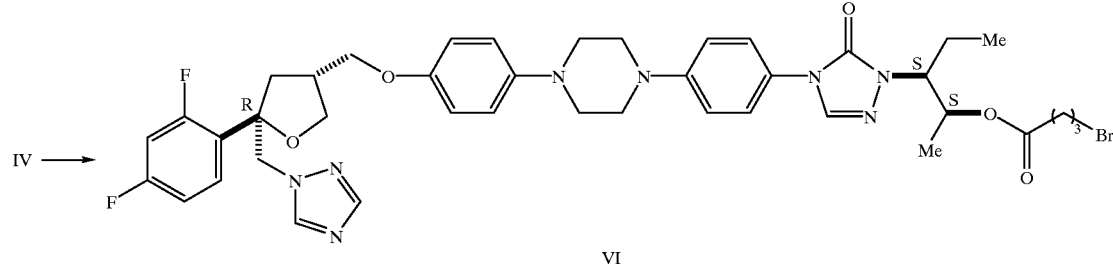

VI

To a stirred mixture of 10 g (14 mmol) of the compound of formula IV (prepared in accordance with the procedure of Example 32 of WO 96/38443, published December 5, 1996) and 2.27 g, (1.3 eq) of the base, 4-(N,N-dimethylamino) pyridine ("DMAP") in 200 mL of methylene chloride, 4-bromobutyryl chloride (1.3 eq, 18.6 mmol, 3.44 g) was added dropwise and the resulting reaction mixture was stirred at room temperature until the reaction was determined to be complete by thin layer chromatography ("TLC"). The reaction mixture was partitioned between saturated aqueous sodium bicarbonate and ethyl acetate ("EtOAc"). The organic phase was separated, washed with water and dried over $MgSO_4$. The organic solvent was removed and the so-formed residue was purified on a silica gel chromatography column using EtOAc as the eluent to provide 8.58 g of the bromide VI as a white solid.

To a stirred solution of the bromide VI of Step A (3.44 g, 4.0 mmol) in 200 ml of dry benzene was added, silver dibenzylphosphate (available from Sigma Chemical Co., St. Louis) (2.0 eq, 8.2 mmol, 3.14 g) and the resulting reaction mixture was heated to reflux for a period of 20 hours. The reaction mixture was cooled and filtered and the filtrate was partitioned between EtOAc and 10% aqueous HCl. The organic phase was separated, washed with water, dried over $MgSO_4$ and concentrated under reduced pressure to provide a residue. The residue was purified on silica gel chromatographic column using EtOAc: MeOH (20:1 (v/v)) as eluent to provide 0.976 g of the starting material bromide VI and 1.221 g of the desired dibenzylphosphate VII as a light brown solid.

Step (B)

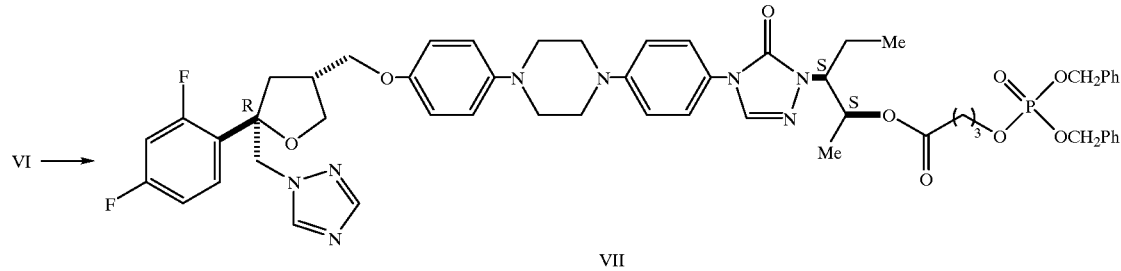

VII

Step (C)

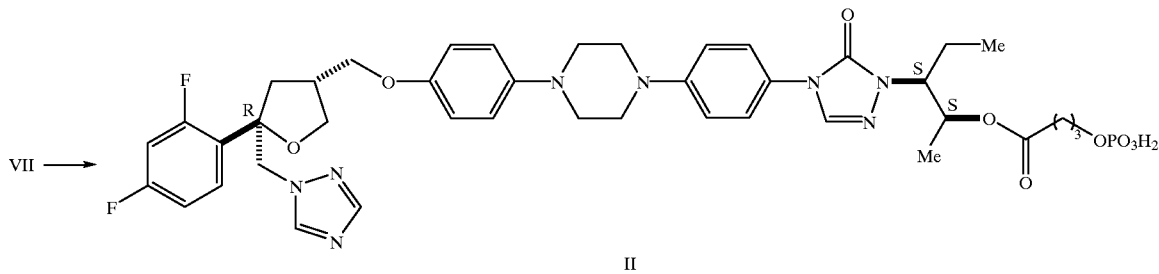

A stirred suspension of 10% Pd on carbon (0.60 g) and the dibenzylphosphate VII (1.2 g 1.14 m mol) of step B in EtOH (40 mL) and acetic acid("HOAc") (40 mL) was placed under an atmosphere of hydrogen gas at room temperature overnight (or 16 hours). The reaction mixture was then filtered through a pad of celite and the solid pad was washed thoroughly with methanol. The combined filtrates were concentrated under reduced pressure to yield 0.976 g of the compound II as a light brown solid. $^1$H nmr: $\delta_H$ (CD$_3$OD), 8.38 (s,1), 8.06 (s, 1), 7.77 (s,1), 7.42–7.48(m, 2), 7.34–7.42 (m,1) 7.06–7.23 (m,5), 6.96–7.03 (m,1), 6.83–6.90 (m, 2), 5.13–5.22 (m, 1) 4.67 (s,2), 4.09–4.17 (m, 2), 3.70–3.91 (m, 4), 3.39–3.45 (m, 4), 3.24–3.30 (m, 4), 2.50–2.65 (m, 2), 2.30–2.38 (m, 2), 2.14–2.22 (m, 1), 1.74–1.98 (m,4), 1.30 (d, 3) and 0.88 (t, 3).

FABMS (Found: [MH$^+$]867.3404; Calcd :[ MH$^+$] 867.3406.

Step (D)

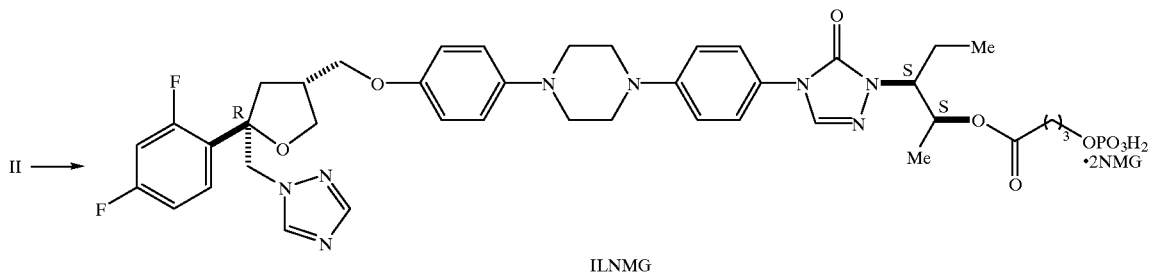

To the product II of step C, (0.940 g, 1.08 mmol) was added N-methylglucamine(2 eq, 2.17 mmol. 0.423 g) in 10 mL of water. The resulting solution was filtered and the filtrate was concentrated under a stream of nitrogen to provide 1.396 g of the di NMG salt represented by the formula II.2NMG as a light brown solid.

$^1$H nmr: $\delta_H$ (CD$_3$OD), 8.37 (s,1), 8.08 (s,1), 7.76 (s,1), 7.42–7.46 (m, 2), 7.34–7.41 (m, 1), 7.11–7.16 (m, 2), 6.96–7.02 (m, 3), 6.80–6.90 (m, 3), 5.14–5.22 (m, 1), 4.66 (s,2), 4.10–4.16 (m, 2), 3.96–4.03 (m, 2), 3.60–3.87 (m, 14), 3.35–3.40 (m, 4), 3.18–3.23 (m, 4), 2.88–3.01 (m, 4), 2.50–2.65 (m, 2), 2.56 (s, 6), 2.34–2.41 (m, 2), 2.15–2.22 (m, 1), 1.76–1.96 (m, 4), 1.30 (d, 3) and 0.87 (t, 3).

EXAMPLE 2

Preparation of the Compound of Formula III:2(S)-[4-{4-{4-{4-[[(R-Cis)-2-(2,4-difluorophenyl)-tetrahydro-2-(1H-1,2,4-triazol-1-ylmethyl)-4-furanyl]methoxy]phenyl]-1-piperazinyl]phenyl]-4,5-dihydro-5-oxo-1H-1,2,4-triazol-1-yl]-1-(S)-methylbutyl-4-hydroxy-butanoate Step (A)

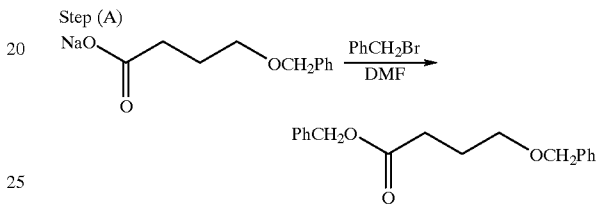

To a stirred suspension of 0.29 g of a 60% dispersion of sodium hydride in mineral oil (1 eq, 0.19 g, of sodium hydride) in 5 mL of dimethyl formamide ("DMF") at room temperature under an atmosphere of nitrogen was added 1.00 g (7.7 mmol) of 4-hydroxybutyric acid, sodium salt. The so-formed reaction mixture was stirred for 30 minutes and 1.36 g (1 eq, 0.94 mL) of benzyl bromide was added. The resulting reaction mixture was stirred overnight. After an aqueous workup, the crude product was isolated and purified on a silica gel chromatography column using ETOAc-hexane (1:20, v/v) as an eluent to produce 0.271 g of the benzyl ester, benzyl 4-benzyloxybutyrate.

Step (B)

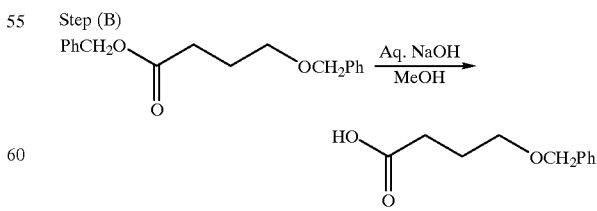

Sodium hydroxide (2, eq, 1.9 mmol, 73 mg) was added in one portion to a stirred mixture of 0.27 g (0.95 m mol) of the benzyl ester from Step (A) in a solution of 3 mL of methanol and 1 mL of water. The so-formed mixture was stirred for 3 hrs. and then concentrated under reduced pressure. The so-formed residue was partitioned between diethyl ether (Et$_2$O) and water. The aqueous phase was separated, washed with Et$_2$O, acidified with aqueous HCl and CH$_2$Cl$_2$ was added. The organic phase was dried over MgSO$_4$ and concentrated to give 0.153 g of 4-benzyloxybutyric acid as a colorless oil.

To a stirred solution of 1.0 g of benzyl ether VIII (prepared in accordance with Step (C) of Example 2) and 1 mL of formic acid in 40 mL of methanol was added 0.5 g of palladium black catalyst. The so-formed reaction mixture was heated to reflux for 15 min. The reaction mixture was cooled to room temperature and the Pd catalyst was removed Step (C)

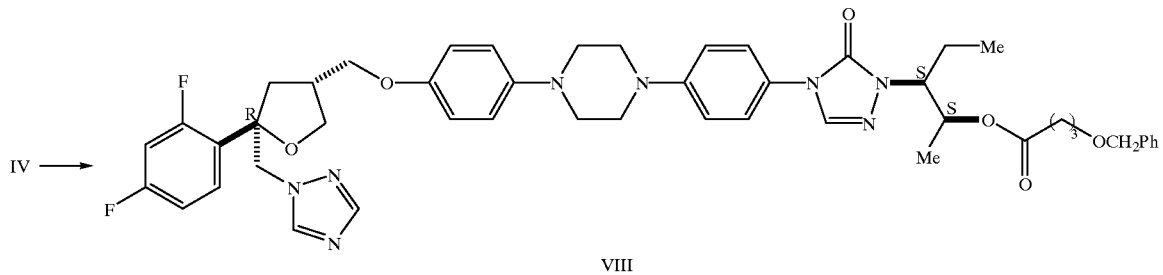

To a stirred mixture of 1.0 g of 4-benzyloxybutyroic acid from Step (B) 0.507 mmol, 3.62 g of the compound of formula IV (prepared in accordance with the procedure of Example 32 of WO 96/38443, published Dec. 5, 1996) and 0.82 g of the base, 4-(N,N-dimethylamino)pyridine ("DMAP") in 50 mL of methylene chloride, 1.26 g of dicyclohexylcarbodimide ("DCC") were added and the resulting reaction mixture was stirred at room temperature until the reaction was determined to be complete (4 hrs) by thin layer chromatography ("TLC"). The reaction mixture was partitioned between 5% aqueous citric acid and EtOAc. The organic phase was separated, washed with water and dried over MgSO$_4$. The organic solvent was removed and the so-formed residue was purified on a silica gel chromatography column using EtOAc as the eluent to provide 2.8 g of the benzyl ether VIII. The H$^1$ NMR was consistent with the structure of VIII.

FABMS (Found :[MH]+, 877.4182 C$_{48}$H$_{55}$N$_8$O$_6$F$_2$ requires 877.4213); [α]$_D^{24}$=(−) 56.5° (c, 1.01; CHCl$_3$); $^1$H nmr: δ$_H$(CDCl$_3$), 8.12 (s,1), 7.80 (s,1), 7.58 (d,1), 7.24–7.43 (m, 8), 6.75–7.01 (m, 8), 5.18–5.27 (m,1), 4.64 (A of AB, 1), 4.52 (B of AB, 1), 4.44 (s, 2), 4.16–4.24 (m,1), 4.09–4.14 (m, 1), 3.76–3.81 (m, 1), 3.68–3.74 (m, 1), 3.59–3.65 (m, 1), 3.41–3.46 (m, 2), 3.30–3.36 (m, 4), 3.18–3.24 (m,4), 2.51–2.66 (m,2), 2.34–2.40 (m, 2), 2.05–2.12 (m, 1), 1.74–1.99 (m, 4), 1.29 (d, 3), and 0.89 (t, 3).

by filtration. The filtered catalyst was washed with methanol. The combined methanol fractions were concentrated and purified on a silica gel chromatography column using 5% methanol in EtOAc as an eluent to provide 0.7 g of the alcohol of formula III.

FABMS (Found:[MH]$^+$787.3743. C$_{41}$H$_{49}$N$_8$O$_6$F$_2$ requires 787.3714); [α]$_D^{24}$=(−) 64.80 (c,1.03; CHCl$_3$); $^1$H nmr: δH(CDCl$_3$), 8.11 (s,1), 7.80 (s,1) 7.64(s,1), 7.35–7.45 (m,3), 6.99–7.05 (m,2), 6.89–6.95 (m,2), 6.75–6.89 (m,4), 5.19–5.27 (m,1), 4.65 (A of AB,1), 4.51 (B of AB,1), 4.18–4.24 (m,1), 4.08–4.15 (m,1), 3.75–3.81(m,1), 3.68–3.73 (m,1), 3.53–3.65 (m,3), 3.32–3.40 (m,4), 3.18–3.26 (m,4), 2.51–2.66 (m,2), 2.34–2.41 (m,2), 2.04–2.12 (m,1), 1.88–1.99 (m,1), 1.74–1.84 (m,3), 1.32 (d,3) and 0.90 (t,3).

Step (D)

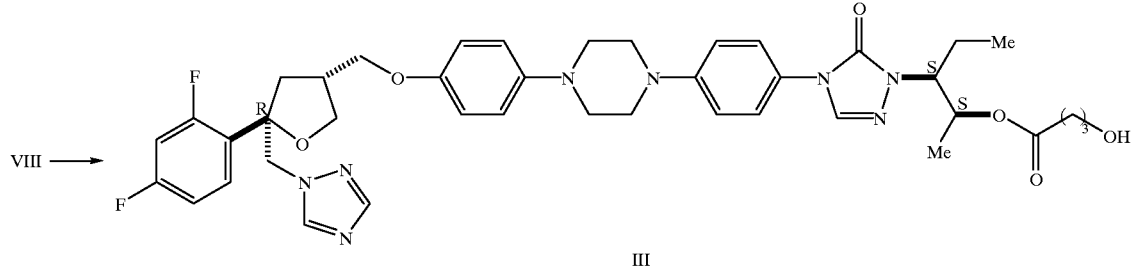

Step (E)

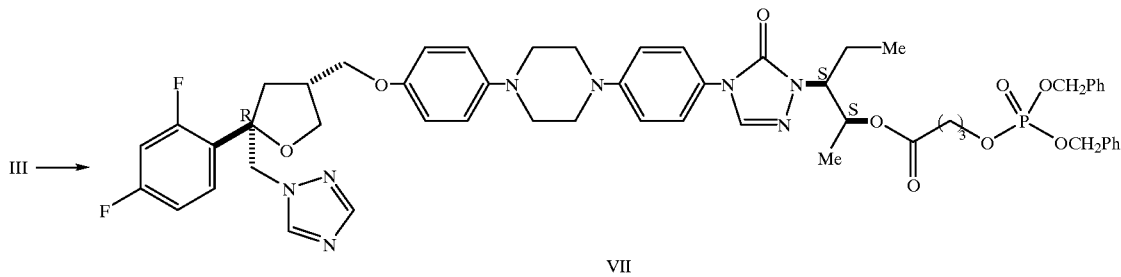

VII

To a stirred solution of the alcohol III (0.140 g, 0.18 mmol.) of Step(D) of Example 2 and tetrazole (0.53 mmol, 3 eq, 0.037 g) in 5 mL of $CH_2Cl_2$, N,N-diisopropyidibenzylphosphoramidite (1.5 eq, 0.27 mmol, 0.0922 g) was added dropwise and the so-formed reaction mixture was stirred at room temperature for a period of 1 hr. A solution of tertbutylhydroperoxide (3 eq, 90 μL of a 5.5 molar solution in iso-octanol) was then added to the stirred reaction mixture the stirring was maintained for 3 additional hours. The so-formed reaction mixture was partitioned between a 10% aqueous sodium thiosulfate solution and ethanol. The organic phase was separated, washed with saturated sodium bicarbonate and dried over anhydrous sodium sulfate. The organic phase was concentrated and purified on a silica gel chromatography column using EtOAc-methanol (20:1, v/v) as an eluent to give 0.1389 g of the dibenzylphosphate compound having a structure by $^1H$ nmr consistent with that of formula VII of Step B of Example 1.

Step (F)

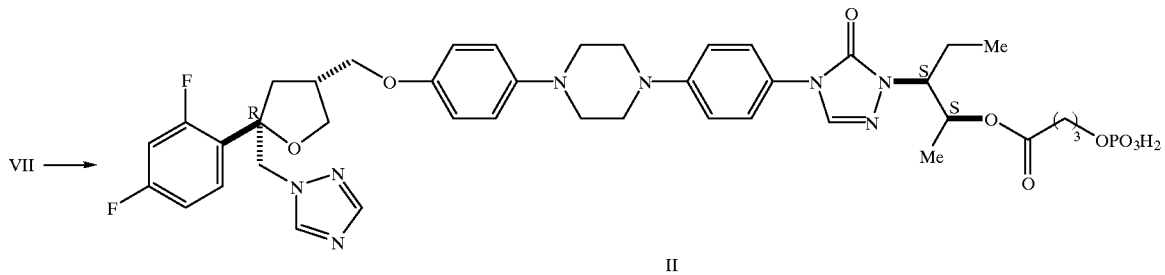

II

The compound VII of Step(C) of Example 2 was treated in accordance with the procedure of Step(C) of Example 1 to give the title compound of formula II.

What is claimed is:

1. A compound represented by the formula III:

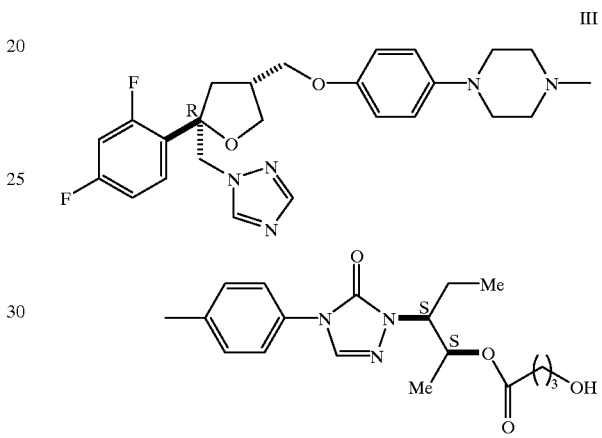

III or a pharmaceutically acceptable salt thereof.

2. A pharmaceutical composition comprising an antifungally effective amount of the compound of claim 1 and a pharmaceutically acceptable carrier.

3. The pharmaceutical composition of claim 2 adapted for parenteral administration.

4. A method of treating or preventing a fungal infection in a host which comprises administering to said host an antifungally effective amount of the compound of claim 1.

5. A method of treating or preventing a fungal infection in a host which comprises parenterally administering to said host an antifungally effective amount of the compound of claim 1.

* * * * *